United States Patent [19]
Ptchelintsev

[11] Patent Number: 5,607,968
[45] Date of Patent: Mar. 4, 1997

[54] TOPICAL ALKYL-2-O-L-ASCORBYL-PHOSPHATES

[75] Inventor: Dmitri Ptchelintsev, Mahwah, N.J.

[73] Assignee: Avon Products, Inc., Suffern, N.Y.

[21] Appl. No.: 487,957

[22] Filed: Jun. 7, 1995

[51] Int. Cl.$^6$ .............................. A01N 43/08; A61K 31/34
[52] U.S. Cl. .......................... 514/474; 514/844; 514/847; 424/401; 549/315
[58] Field of Search ................................ 514/474, 844, 514/847; 424/401; 549/315

[56] References Cited

U.S. PATENT DOCUMENTS

| | | |
|---|---|---|
| 3,151,127 | 9/1964 | Spanel . |
| 4,564,686 | 1/1986 | Ogata . |
| 4,939,128 | 7/1990 | Kato et al. . |
| 5,078,989 | 1/1992 | Ando et al. ............................. 514/474 |
| 5,306,713 | 4/1994 | Suetsugu et al. . |
| 5,508,275 | 4/1996 | Weithmann et al. .................. 514/474 |

FOREIGN PATENT DOCUMENTS 0503582  9/1992  European Pat. Off. .

OTHER PUBLICATIONS

Menon et al., *Structural Basis for the Barrier Abnormality Following Inhibition of HMG CoA Reductase in Murine Epidermis*, J. Invest. Dermatol., vol. 98, pp. 209–219 (1992).

Steinhart et al., *Pro–and Antioxidative Effect of Ascorbic Acid on L–Tryptophan in the System $Fe^{3+}$/Ascorbic Acid/$O_2$*, J. Agric. Food Chem., vol. 41, pp. 2275–2277 (1993).

Sakamoto et al., *Measurement Method of Efficacy of Antidandruff Cosmetics and Development of the New Active Commercial Product*, IFSCC, Yokohama, vol. B206, pp. 823–864 (1993).

*Primary Examiner*—Nathan M. Nutter
*Attorney, Agent, or Firm*—Hopgood, Calimafde, Kalil & Judlowe L.L.P.

[57] ABSTRACT

This disclosure relates to a method for topical use of a derivative of L-ascorbic acid which is stable, easily incorporated into cosmetically acceptable vehicles and enzymatically bioreversible in the skin to free ascorbic acid and a safe alkanol component. An exemplary embodiment uses the alkyl-2-O-L-ascorbyl-phosphate which is shown in Formula I.

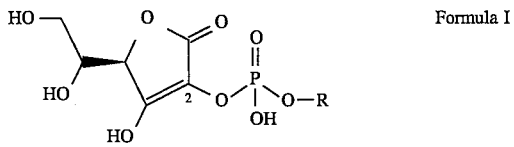

Formula I

10 Claims, No Drawings

TOPICAL ALKYL-2-O-L-ASCORBYL-PHOSPHATES

FIELD OF THE INVENTION

The present invention relates to the topical use of a novel derivative of L-ascorbic acid that is stable, easily incorporated into cosmetically acceptable vehicles and enzymatically bioreversible to its constituent components. Exemplary derivatives used topically include a 2-O-L-ascorbyl-phosphate in which the phosphate group is derivatized with a straight chain alkyl group having 2 to 18 carbons ($C_2$–$C_{18}$) and salts thereof.

BACKGROUND OF THE RELATED ART

The use of L-ascorbic acid as an anti-oxidant in food preparations is known. For example, Steinhart, Pro- and Antioxidative Effect of Ascorbic Acid on L-Tryptophan in the System $Fe^{3+}$/Ascorbic Acid/$O_2$, J. Agric. Food Chem., Vol. 41, pages 2275–2277 (1993) describes the use of L-ascorbic acid as an anti-oxidant which performs its function in food by removing free radicals and undergoing rapid oxidation itself.

Similarly, free L-ascorbic acid in topical preparations demonstrates poor stability and tends to break down due to partially oxidative and non-oxidative degradation. The degraded ascorbic acid loses activity and the host product loses aesthetic appeal by exhibiting a brown color which is unacceptable for commercial cosmetics.

U.S. Pat. No. 4,939,128 describes an ingestible ascorbic acid conjugated with different hydrocarbon groups through a phosphate linkage. These compounds are indicated for use as an oral therapeutic for treating ischemic injury to cell tissue of internal organs. The '128 patent specification does not indicate a need for storage stability nor a need for maintaining aesthetic appearances of the disclosed compounds such as required in topical cosmetics.

Attempts have been made to use ascorbic acid conjugated with a glycyrrhetic group as described in European Application No. 92104149.7; and with a tocopheryl group as indicated by U.S. Pat. No. 3,151,127. U.S. Pat. Nos. 4,564,686 and 5,306,713 also disclose tocopheryl ascorbyl phosphate as an anti-oxidant having the following structure.

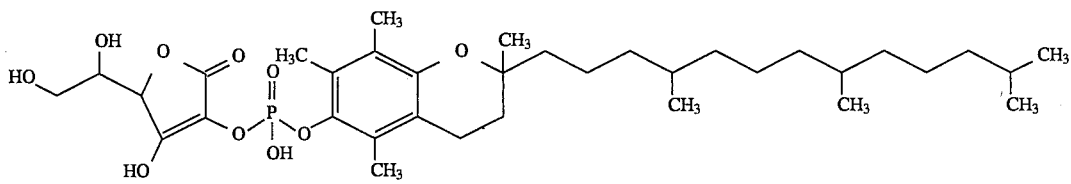

Sakamoto, Measurement Method of Efficacy of Antidandruff Cosmetics and Development of the New Active Commercial Product, IFSCC, Yokohama, Vol. B206, pages 823–864 (1993) describes the use of tocopheryl coupled to L-ascorbic acid. The coupled tocopheryl is an anti-oxidant preservative for the ascorbyl group. None of these teachings provide a method of using a stable, ascorbic acid derivatized with a straight chain alkyl group as a topical agent.

There is a need in the art for a method of using an ascorbic acid derivative having a phosphate linked straight chain alkyl group for improving skin condition and appearance wherein the ascorbic acid is stable, has a long shelf-life and is bioavailable upon topical application even after long term storage.

OBJECTS OF THE INVENTION

Accordingly, it is an object of the present invention to provide a method for topical use of an ascorbic acid derivatized with a straight chain ($C_2$–$C_{18}$) alkyl group for improving skin condition and appearance wherein the ascorbic acid is stable, has a long shelf-life and does not undergo aesthetically unacceptable changes.

A further object of the present invention is to provide a method of topical use for a derivative of ascorbic acid which is stable, easily carried in cosmetic vehicles and enzymatically bio-reversible to free ascorbic acid and a safe, straight-chain alkanol.

These and other objects will become evident from the disclosure provided below.

SUMMARY OF THE INVENTION

The present invention includes a method for using L-ascorbic acid derivatives such as 2-O-L-ascorbyl-phosphate in which the phosphate group is derivatized with a straight chain alkyl group having 2 to 18 carbons. Exemplary compounds include ethyl-2-O-L-ascorbyl-phosphate, propyl-2-O-L-ascorbyl-phosphate, butyl-2-O-L-ascorbyl-phosphate, amyl-2-O-L-ascorbyl-phosphate, hexyl-2-O-L-ascorbyl-phosphate, heptyl-2-O-L-ascorbyl-phosphate, octyl-2-O-L-ascorbyl-phosphate, nonyl-2-O-L-ascorbyl-phosphate, decyl-2-O-L-ascorbyl-phosphate, undecanyl-2-O-L-ascorbyl-phosphate, dodecanyl-2-O-L-ascorbyl-phosphate, tridecanyl-2-O-L-ascorbyl-phosphate, tetradecanyl-2-O-L-ascorbyl-phosphate, pentadecanyl-2-O-L-ascorbyl-phosphate, hexadecanyl-2-O-L-ascorbyl-phosphate, heptadecanyl-2-O-L-ascorbyl-phosphate, and octadecanyl-2-O-L-ascorbyl-phosphate, having the generalized formula illustrated below.

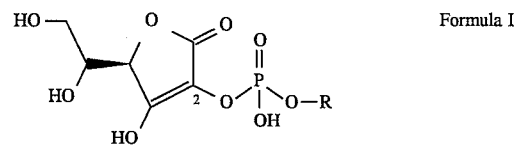

Formula I

An exemplary embodiment is the topical use of dodecanyl-2O-L-ascorbyl-phosphate (lauryl-2-O-L-ascorbyl-phosphate, shown below in Formula II) in a suitable carrier such as a lotion. The dermatologic response to this method is an improvement to the skin condition and appearance, and the method finds merit in cosmetic application as the ascorbic acid derivatives described herein are stable, have long shelf-lives and do not undergo aesthetically unacceptable changes such discolorations or malodor.

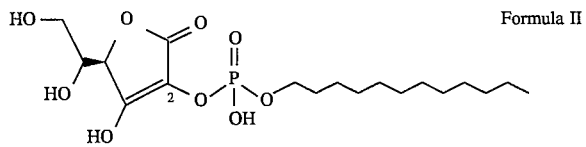

Formula II

The novel method takes advantage of the covalent and bioreversible coupling of the alkyl-2-O-L-ascorbyl-phosphate to L-ascorbic acid which results in stabilization of and increased bioavailability for the ascorbic acid. In the alkyl-2-O-L-ascorbyl-phosphate compounds used, the conjugated ascorbic acid becomes resistant to degradation. The straight-chain alkyl group serves as a carrier moiety and facilitates delivery of the ascorbic acid through the outermost protective layer of skin (i.e., the stratum corneum) and increases the bioavailability of the ascorbic acid in the topical application.

Natural enzymes, such as phosphatases present in the skin, gradually cleave the phosphate linkage between the alkyl group and the ascorbic acid, resulting in sustained release of free L-ascorbic acid into the stratum corneum. The released straight-chain alkanol groups are basic organic compounds which serve as natural substrates for skin.

A typical formulation used in the present invention can comprise a $C_2$–$C_{18}$ alkyl group coupled to L-ascorbyl-phosphate, such as a compound selected from the group consisting of ethyl-2-O-L-ascorbyl-phosphate, propyl-2-O-L-ascorbyl-phosphate, butyl-2-O-L-ascorbyl-phosphate, amyl-2-O-L-ascorbyl-phosphate, hexyl-2-O-L-ascorbyl-phosphate, heptyl-2-O-L-ascorbyl-phosphate, octyl-2-O-L-ascorbyl-phosphate, nonyl-2-O-L-ascorbyl-phosphate, decyl-2-O-L-ascorbyl-phosphate, undecanyl-2-O-L-ascorbyl-phosphate, dodecanyl-2-O-L-ascorbyl-phosphate, tridecanyl-2-O-L-ascorbyl-phosphate, tetradecanyl-2-O-L-ascorbyl-phosphate, penta-decanyl-2-O-L-ascorbyl-phosphate, hexadecanyl-2-O-L-ascorbyl-phosphate, heptadecanyl-2-O-L-ascorbyl-phosphate, and octadec-anyl-2-O-L-ascorbyl-phosphate in a suitable topical vehicle. In addition, ammonium, calcium, lithium, potassium or sodium salts of these compounds are readily incorporated into cosmetically acceptable vehicles. A salt with an organic amine such as ethanolamine will also provide the benefits intended by this invention.

Suitable vehicles include conventional lotions, creams or gels. A lotion embodiment may comprise about 0.1 to about 20.0% alkyl-2-O-L-ascorbyl-phosphate, about 0.5 to about 6.0% glycerin, about 2.0 to about 8.0% propylene glycol dicaprylate/dicaprate, about 1.8 to about 4.0% Peg 40 Stearate, about 1.0 to about 2.5% Steareth-2, about 0.25 to about 0.7% xanthan gum, about 0.25 to about 0.7% hydroxyethyl cellulose, about 0.15 to about 0.2% disodium EDTA and about 0.20 to about 0.25% methylparaben with all ranges expressed as weight percents.

A cream embodiment may comprise about 0.1 to about 20.0% alkyl-2-O-L-ascorbyl-phospahte, about 0.5 to about 4.0% glycerin, about 2.0 to about 6.0% propylene glycol dicaprylate/dicaprate, about 1.8 to about 3.0% Steareth-20, about 0.8 to about 2.0% Steareth-2, about 0.25 to about 0.6% xanthan gum, about 0.25 to about 0.6% hydroxyethyl cellulose, about 1.0 to about 2.5% cetyl alcohol, about 0.9 to about 3.5% glycerol mono-stearate and about 0.15 to about 0.2% disodium EDTA.

A gel embodiment may comprise about 0.1 to about 20.0% alkyl-2-O-L-ascorbyl-phosphate, about 0.15 to about 0.2% disodium EDTA, about 2.0 to about 6.0% propylene glycol, about 0.4 to about 1.5% hydroxyethyl cellulose and about 0.20 to about 0.25% methylparaben.

The pH of these formulations can be adjusted to physiologically acceptable levels with sufficient amounts of ammonium hydroxide, calcium hydroxide, lithium hydroxide, potassium hydroxide, sodium hydroxide, ethanolamine, diethanolamine or urea.

DETAILED DESCRIPTION OF THE INVENTION

The compounds used in the topical method of the present invention are generally synthesized following the procedure outlined in Example 1. The derivatives are stable in solution, exhibit anti-oxidant activity and stimulate production of collagen in fibroblasts.

EXAMPLE 1

Synthesis of Lauryl-2-O-L-Ascorbyl-Phosphate

Initially, 5,6-O-isopropylidene-L-ascorbic acid (IAA) was prepared by adding L-ascorbic acid (100 gm, 0.57 mole) into a three-necked 1-liter flask equipped with a mechanical stirrer and a thermometer. The L-ascorbic acid was followed by acetone (450 ml) and acetyl chloride (12.5 ml), and the whole mixture was stirred vigorously at 30°–40° C. for 2 hours.

The mixture was then allowed to sit at room temperature overnight and the colorless crystals were collected by filtration, washed with cold acetone-hexane mixture (4:7 v/v/; 2×150 ml) and dried under vacuum over potassium hydroxide pellets at 50° C. to give IAA, 97 gm, in 79% yield, m.p. 214°–218° C. ($^1$HNMR-1), cf: m.p. 217°–223° C. in Lee et al., *Carbohydrate Research*, 67:127–138 (1978). The filtrate on evaporation gave a yellowish residue which on crystallization from ethyl acetate (200 ml) gave additional colorless material, which is a mixture of ascorbic acid and IAA.

Lauryl dichlorophosphate was next made by initially adding $POCl_3$ (38.325 gm, 250 mmol) into a 500 ml flame-dried, three-necked flask equipped with a mechanical stirrer, a dropping funnel, a thermometer and a nitrogen inlet tube, followed by dry toluene (distilled over $CaH_2$, 150 ml). The stirred solution was cooled to −10° C. and to it was added dropwise a 1:1 molar solution of lauryl alcohol (46.585 gm, 250 mmol) and triethylamine (25.25 gm, 250 mmol) so that the temperature of the reaction mixture did not go above 5° C.

The reaction mixture was stirred at 0°–5° C. for 90 min and then for a further 90 min at room temperature. The triethylamine hydrochloride that precipitated out from the reaction mixture was removed by filtration under nitrogen using a vacuum pump, and the resulting solid cake was washed with toluene 2×25 ml.

The toluene solution of dodecyl (lauryl) dichlorophosphate thus obtained, was used as such for the reaction with IAA, noted below. Five (5) ml of the above toluene solution on evaporation under vacuum gave 1.68 gm of lauryl dichloro-phosphate, which is equivalent to 55 mmol ($^1$H-NMR-2). Thus, the strength of the toluene solution is 1.1 mmol/1 ml.

Lauryl 2-O-ascorbyl phosphate was next made using a 250 ml flame-dried, three-necked flask under nitrogen equipped with a mechanical stirrer, a thermometer and a dropping funnel, by adding IAA (10.8 gm, 50 mmol) followed by dry toluene (100 ml). The resulting slurry was stirred at room temperature. Triethylamine (10.1 gm, 100 mmol) was added to the stirred mixture over 5 minutes and the whole mixture was stirred at room temperature for 30 minutes (the slurry became thicker at the start of the addition of triethylamine, then became very thin after stirring for 30 minutes).

The reaction mixture was cooled to −10° C. and to it was slowly added the above prepared solution of lauryl dichlorophosphate in toluene (41 ml, 45 mmol) dropwise so that the temperature did not go above 5° C. (the reaction is exothermic and the addition took ~20 minutes).

The reaction mixture was stirred at −5° to 5° C. for 2 hrs at which time the color of the solution had turned pink. Water (50 ml) was added to the reaction mixture and stirring was continued for 10 minutes (the color of the solution became light brown). The organic layer was then separated and the aqueous layer was extracted with toluene (15 ml) and the combined organic extracts were evaporated. The residue was dissolved in 95% ethanol (40 ml) and heated with 1M-hydrochloric acid (40 ml) at 50°–55° C. for 2 hrs. Even without heating, the product, as judged from its NMR ($^1$H) appeared mainly to be the 2-isomer, lauryl 2-O-ascorbyl phosphate. The solvent, mainly ethanol, was removed on rotary evaporator and to the residue, which contained about 15 ml of aqueous hydrochloric acid, was added ethyl acetate (40 ml).

The solution was stirred for a few minutes and the organic layer was separated. The aqueous layer was extracted with ethyl acetate (25 ml) and the combined organic extracts were washed with 15% aqueous sodium chloride solution (3×5 ml) dried over magnesium sulfate (10 gm), treated with charcoal G-60 (300 mg), filtered through celite and evaporated on a rotary evaporator keeping the water bath temperature ~40°–45° C. The residue was a light brown thick syrup, ~23 gm of crude lauryl 2-O-ascorbyl phosphate ($^1$HNMR-3).

The disodium salt of lauryl 2-O-ascorbyl phosphate ascorbate was made by initially taking the crude lauryl 2-O-ascorbyl phosphate (23 gm) and dissolving it in 95% ethanol (50 ml) followed by 25% aqueous sodium hydroxide solution added slowly until the pH of the solution was 9.3 (needed ~13 ml of the 6.25 molar solution). The solvent was evaporated on a rotary evaporator and azeotroped with toluene (2×30 ml).

The residue was dried under vacuum at ~40°to 50° C. over $P_2O_5$ to give the disodium salt, which on pulverization, gave a pale yellow, non-crystalline solid (20 gm) in 95% yield ($^1$HNMR-4) based upon lauryl dichlorophosphate. HPLC of this material shows the purity level ~86% (see HPLC-1). Alternatively, if the solid is triturated with absolute ethanol, the purity level of the disodium salt was increased to ~90% (see HPLC-2), but the yield decreased to 50–55%.

EXAMPLE 2

Fibroblast Studies

This example summarizes a study in which the ability of the alkyl-2-O-L-ascorbyl-phosphates used in the present invention to stimulate collagen production in cultured human skin fibroblasts is demonstrated. An art-recognized [$^3$H]-Proline Incorporation Assay is performed with different doses of lauryl-2-O-L-ascorbyl-phosphate. Juva, *Anal. Biochem.*, 15:77–83 (1966); Booth, *Biochim. Biophys. Acta*, 675:117–122 (1981).

Fibroblasts are incubated with 0 μg/ml, 11.3 μg/ml, 22.5 μg/ml and 45 μg/ml of lauryl-2-O-L-ascorbyl-phosphate for a total of 48 hours. After the first 24 hours [$^3$H]-labeled proline is added to the culture. Following the second 24 hour period the cells are harvested and prepared for the collagen biosynthesis assay.

Protease inhibitors are added to prevent degradation of collagen and other proteins. The cell layer is scraped into a solution containing 0.4M NaCl and 0.01M Tris (pH 7.5).

Extracts are sonicated to disrupt cell membranes. Separate volumes of the cell-containing solution (1 ml each) are dialyzed overnight against several changes of deionized water. The retentate is removed from dialysis and hydrolyzed in 6N hydrochloric acid at 120° C. overnight. The assay is performed using an oxidation process with 2M chloramine-T. Samples are analyzed for radioactive counts, which represent the amount of newly synthesized [$^3$H]-hydroxyproline—an index for new collagen synthesis. Lauryl-2-O-L-ascorbyl-phosphate increases production of new collagen by human skin fibroblasts in a dose-dependent manner.

Various modifications and alterations to the present invention may be appreciated based on a review of this disclosure. These changes and additions are intended to be within the scope and spirit of this invention as defined by the following claims.

What is claimed is:

1. A method for stimulating collagen production in human skin fibroblasts which comprises applying to said human skin a suitable topical vehicle contining from about 0.to about 20% of a compound having the following structure or a salt thereof:

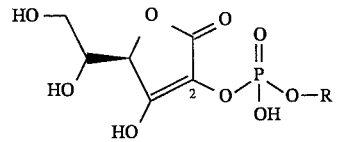

where R is a straight chain $C_2$–$C_{18}$ alkyl group.

2. The method of claim 1, wherein said compound is selected from the group consisting of ethyl-2-O-L-ascorbyl-phosphate, propyl-2-O-L-ascorbyl-phosphate, butyl-2-O-L-ascorbyl-phosphate, amyl-2-O-L-ascorbyl-phosphate, hexyl-2-O-L-ascorbyl-phosphate, heptyl-2-O-L-ascorbyl-phosphate, octyl-2-O-L-ascorbyl-phosphate, nonyl-2-O-L-ascorbyl-phosphate, decyl-2-O-L-ascorbyl-phosphate, undecanyl-2-O-L-ascorbyl-phosphate, dodecanyl-2-O-L-ascorbyl-phosphate, tridecanyl-2-O-L-ascorbyl-phosphate, tetradecanyl-2-O-L-ascorbyl-phosphate, pentadecanyl-2-O-L-ascorbyl-phosphate, hexadecanyl-2-O-L-ascorbyl-phosphate, heptadecanyl-2-O-L-ascorb-yl-phosphate and octadecanyl-2-O-L-ascorbyl-phosphate alkyl-2-L-ascorbly-phosphate.

3. The method of claim 1, wherein said salt is selected from the group consisting of salts of ammonium, calcium, lithium, potassium, sodium and an organic amine.

4. The method of claim 1, wherein said vehicle is selected from the group consisting of a lotion, cream and gel.

5. A topical formulation which comprises:

(a) about 0.1 to about 20.0% of a compound is selected from the group consisting of ethyl-2-O-L-ascorbyl-phosphate, propyl-2-O-L-ascorbyl-phosphate, butyl-2-O-L-ascorbyl-phosphate, amyl-2-O-L-ascorbyl-phosphate, hexyl-2-O-L-ascorbyl-phosphate, heptyl-2-O-L-ascorbyl-phosphate, octyl-2-O-L-ascorbyl-phosphate, nonyl-2-O-L-ascorbyl-phosphate, decyl-2-O-L-ascorbyl-phosphate, undecanyl-2-O-L-ascorbyl-phosphate, dodecanyl-2-O-L-ascorbyl-phosphate, tridecanyl-2-O-L-ascorbyl-phosphate, tetradecanyl-2-O-L-ascorbyl-phosphate, pentadecanyl-2-O-L-ascorbyl-phosphate, hexadecanyl-2-O-L-ascorbyl-phosphate, heptadecanyl-2-O-L-ascorbyl-phosphate and octadecanyl-2-O-L-ascorbyl-phosphate alkyl-2-O-L-ascorbyl-phosphate (b) about 0.5 to about 6.0% glycerin;

(c) about 2.0 to about 8.0% propylene glycol dicaprylate/dicaprate;

(d) about 1.8 to about 4.0% Peg 40 Stearate;

(e) about 1.0 to about 2.5% Steareth-2;

(f) about 0.25 to about 0.7% xanthan gum;

(g) about 0.25 to about 0.7% hydroxyethyl cellulose;

(h) about 0.15 to about 0.2% disodium EDTA; and (i) about 0.20 to about 0.25% methylparaben.

6. The topical formulation of claim 5, wherein the pH of said formulation is adjusted to physiologically acceptable levels with sufficient amounts of a compound selected from the group consisting of ammonium hydroxide, calcium hydroxide, lithium hydroxide, potassium hydroxide, sodium hydroxide, ethanolamine, diethanolamine and urea.

7. A topical formulation which comprises:

(a) about 0.1 to about 20.0% of a compound is selected from the group consisting of ethyl-2-O-L-ascorbyl-phosphate, propyl-2-O-L-ascorbyl-phosphate, butyl-2-O-L-ascorbyl-phosphate, amyl-2-O-L-ascorbyl-phosphate, hexyl-2-O-L-ascorbyl-phosphate, heptyl-2-O-L-ascorbyl-phosphate, octyl-2-O-L-ascorbyl-phosphate, nonyl-2-O-L-ascorbyl-phosphate, decyl-2-O-L-ascorbyl-phosphate, undecanyl-2-O-L-ascorbyl-phosphate, dodecanyl-2-O-L-ascorbyl-phosphate, tridecanyl-2-O-L-ascorbyl-phosphate, tetradecanyl-2-O-L-ascorbyl-phosphate, pentadecanyl-2-O-L-ascorbyl-phosphate, hexadecanyl-2-O-L-ascorbyl-phosphate, heptadecanyl-2-O-L-ascorbyl-phosphate and octadecanyl-2-O-L-ascorbyl-phosphate alkyl-2-O-L-ascorbyl-phosphate;

(b) about 0.5 to about 4.0% glycerin;

(c) about 2.0 to about 6.0% propylene glycol dicaprylate/dicaprate;

(d) about 1.8 to about 3.0% Steareth-20;

(e) about 0.8 to about 2.0% Steareth-2;

(f) about 0.25 to about 0.6% xanthan gum;

(g) about 0.25 to about 0.6% hydroxyethyl cellulose;

(h) about 1.0 to about 2.5% cetyl alcohol;

(i) about 0.9 to about 3.5% glycerol mono-stearate; and (j) about 0.15 to about 0.2% disodium EDTA.

8. The topical formulation of claim 7, wherein the pH of said formulation is adjusted to physiologically acceptable levels with sufficient amounts of a compound selected from the group consisting of ammonium hydroxide, calcium hydroxide, lithium hydroxide, potassium hydroxide, sodium hydroxide, ethanolamine, diethanolamine and urea.

9. A topical formulation which comprises:

(a) about 0.1 to about 20.0 of a compound is selected from the group consisting of ethyl-2-O-L-ascorbyl-phosphate, propyl-2-O-L-ascorbyl-phosphate, butyl-2-O-L-ascorbyl-phosphate, amyl-2-O-L-ascorbyl-phosphate, hexyl-2-O-L-ascorbyl-phosphate, heptyl-2-O-L-ascorbyl-phosphate, octyl-2-O-L-ascorbyl-phosphate, nonyl-2-O-L-ascorbyl-phosphate, decyl-2-O-L-ascorbyl-phosphate, undecanyl-2-O-L-ascorbyl-phosphate, dodecanyl-2-O-L-ascorbyl-phosphate, tridecanyl-2-O-L-ascorbyl-phosphate, tetradecanyl-2-O-L-ascorbyl-phosphate, pentadecanyl-2-O-L-ascorbyl-phosphate, hexadecanyl-2-O-L-ascorbyl-phosphate, heptadecanyl-2-O-L-ascorb-yl-phosphate and octadecanyl-2-O-L-ascorbyl-phosphate alkyl-2-O-L-ascorbyl-phosphate;

(b) about 0.15 to about 0.2% disodium EDTA;

(c) about 2.0 to about 6.0% propylene glycol;

(d) about 0.4 to about 1.5% hydroxyethyl cellulose; and (e) about 0.20 to about 0.25% methylparaben.

10. The topical formulation of claim 9, wherein the pH of said formulation is adjusted to physiologically acceptable levels with sufficient amounts of a compound selected from the group consisting of ammonium hydroxide, calcium hydroxide, lithium hydroxide, potassium hydroxide, sodium hydroxide and ethanolamine.

\* \* \* \* \*